United States Patent [19]

Holton

[11] Patent Number: 5,254,703
[45] Date of Patent: Oct. 19, 1993

[54] SEMI-SYNTHESIS OF TAXANE DERIVATIVES USING METAL ALKOXIDES AND OXAZINONES

[75] Inventor: Robert A. Holton, Tallahassee, Fla.

[73] Assignee: Florida State University, Tallahassee, Fla.

[21] Appl. No.: 863,829

[22] Filed: Apr. 6, 1992

[51] Int. Cl.$^5$ ............................................ C07D 305/14
[52] U.S. Cl. ...................... 549/510; 549/511
[58] Field of Search ................... 549/510, 511

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 849/510 |
| 4,924,012 | 5/1990 | Colin et al. | 849/510 |
| 4,942,184 | 7/1990 | Haugwitz et al. | 514/449 |
| 5,015,744 | 5/1991 | Holton | 549/510 |

FOREIGN PATENT DOCUMENTS

| | | |
|---|---|---|
| 253738 | 7/1987 | European Pat. Off. . |
| 253739 | 7/1987 | European Pat. Off. . |
| 336840 | 4/1989 | European Pat. Off. . |
| 336841 | 4/1989 | European Pat. Off. . |

OTHER PUBLICATIONS

Dennis et al., "A Highly Efficient, Practical Approach to Natural Taxol", J. Am. Chem. Soc. 1988, 110, 5917–5919.

Holton et al., "A Synthesis of Taxusin", J. Am. Chem. Soc., 1988, 110, pp. 6558–6560.

Holton, "Synthesis of the Taxane Ring System", J. Am. Chem. Soc., 1984, 106, pp. 5731–5732.

March, "Advanced Organic Chemistry", 3rd Ed. p. 351, Reaction 0–25, (1985).

Wani et al., "Plant Antitumor Agents. VI. The Isolation and Structure of Taxol, a Novel Antileukemic and Antitumor Agent from Taxus Brevifolia", J. Am. Chem. Soc. 93:9, May 5, 1971, pp. 2325–2327.

Mukerjee et al., "β-Lactams: Retrospect and Prospect", Tetrahedron vol. 34, Report No. 52, pp. 1731–1767 (1978).

Primary Examiner—C. Warren Ivy
Assistant Examiner—Ba K. Trinh
Attorney, Agent, or Firm—Senniger, Powers, Leavitt & Roedel

[57] ABSTRACT

A process for preparing taxane derivatives taxol by providing a metal alkoxide having the bi, tri-, or tetracyclic taxane nucleus, reacting the metal alkoxide with an oxazinone to form an intermediate, and converting the intermediate to the taxane derivative.

13 Claims, No Drawings

SEMI-SYNTHESIS OF TAXANE DERIVATIVES USING METAL ALKOXIDES AND OXAZINONES

BACKGROUND OF THE INVENTION

The present invention is directed to a semi-synthesis for the preparation of taxane derivatives such as taxol, taxotere and other biologically active derivatives involving the use of metal alkoxides and oxazinones.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has the following structure:

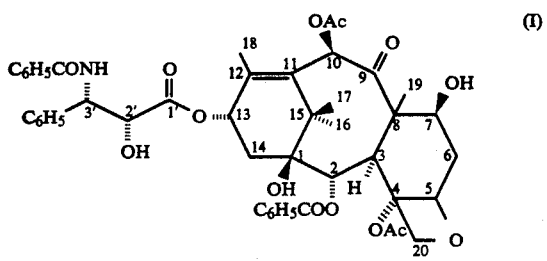

wherein Ac is acetyl. Because of this promising activity, taxol is currently undergoing clinical trials in both France and the United States.

The supply of taxol for these clinical trials is presently being provided by the bark from *Taxus brevifollia* (Western Yew). However, taxol is found only in minute quantities in the bark of these slow growing evergreens, causing considerable concern that the limited supply of taxol will not meet the demand. Consequently, chemists in recent years have expended their energies in trying to find a viable synthetic route for the preparation of taxol. So far, the results have not been entirely satisfactory.

One synthetic route that has been proposed is directed to the synthesis of the tetracyclic taxane nucleus from commodity chemicals. A synthesis of the taxol congener taxusin has been reported by Holton, et al. in JACS 110, 6558 (1988). Despite the progress made in this approach, the final total synthesis of taxol is, nevertheless, likely to be a multi-step, tedious, and costly process.

A semi-synthetic approach to the preparation of taxol has been described by Greene, et al. in JACS 110, 5917 (1988), and involves the use of a congener of taxol, 10-deacetyl baccatin III which has the structure of formula II shown below:

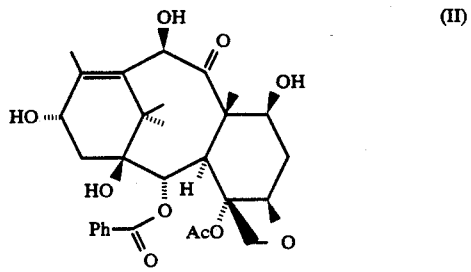

10-deacetyl baccatin III is more readily available than taxol since it can be obtained from the needles of *Taxus baccata*. According to the method of Greene et al., 10-deacetyl baccatin III is converted to taxol by attachment of the C-10 acetyl group and by attachment of the C-13 β-amido ester side chain through the esterification of the C-13 alcohol with a β-amido carboxylic acid unit. Although this approach requires relatively few steps, the synthesis of the β-amido carboxylic acid unit is a multi-step process which proceeds in low yield, and the coupling reaction is tedious and also proceeds in low yield. However, this coupling reaction is a key step which is required in every contemplated synthesis of taxol or biologically active derivative of taxol, since it has been shown by Wani, et al. in JACS 93, 2325 (1971) that the presence of the β-amido ester side chain at C13 is required for anti-tumor activity.

More recently, it has been reported in Colin et al. U.S. Pat. No. 4,814,470 that taxol derivatives of the formula III below, have an activity significantly greater than that of taxol (I).

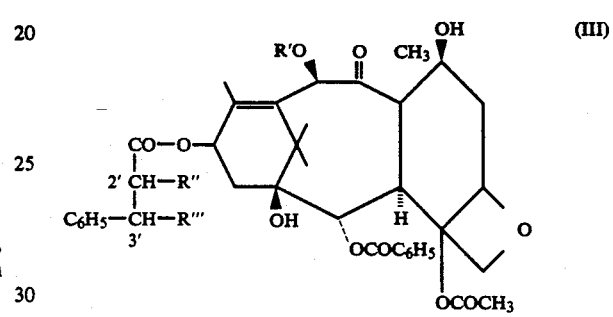

R' represents hydrogen or acetyl and one of R" and R'" represents hydroxy and the other represents tert-butoxycarbonylamino and their stereoisomeric forms, and mixtures thereof.

According to Colin et al., U.S. Pat. No. 4,418,470, the products of general formula (III) are obtained by the action of the sodium salt of tert-butyl N-chlorocarbamate on a product of general formula:

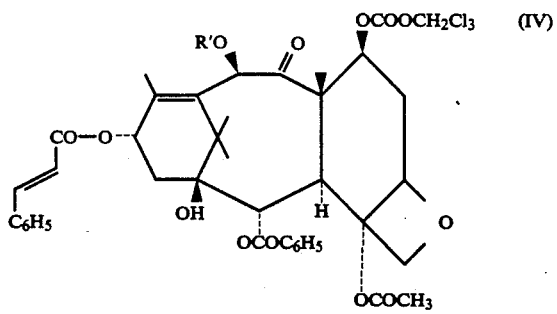

in which R' denotes an acetyl or 2,2,2-trichloroethoxycarbonyl radical, followed by the replacement of the 2,2,2-trichloroethoxycarbonyl group or groups by hydrogen. It is reported by Denis et al. in U.S. Pat. No. 4,924,011, however, that this process leads to a mixture of isomers which has to be separated and, as a result, not all the baccatin III or 10-deactylbaccatin III employed for the preparation of the product of general formula (IV) can be converted to a product of general formula (III).

In an effort to improve upon the Colin et al. process, Denis et al. disclose a different process for preparing derivatives of baccatin III or of 10-deacetylbaccatin III of general formula

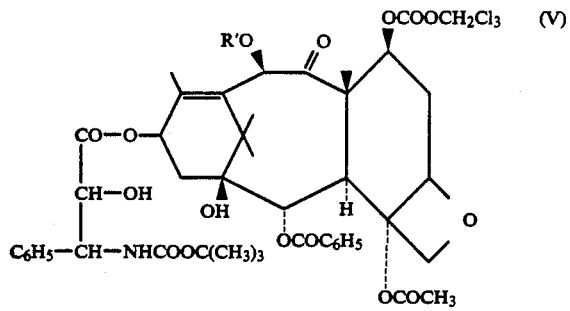

(V)

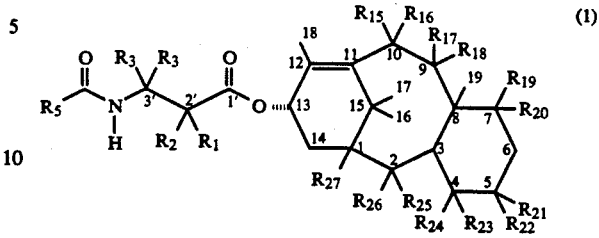

(I)

ically active taxane derivatives having the following structural formula:

in which R' denotes hydrogen or acetyl wherein an acid of general formula:

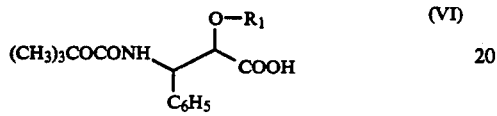

(VI)

in which $R_1$ is a hydroxy-protecting group, is condensed with a taxane derivative of general formula:

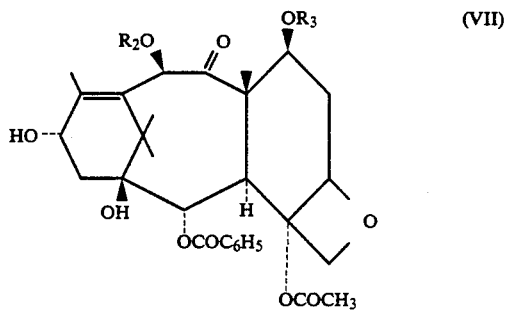

(VII)

in which $R_2$ is an acetyl hydroxy-protecting group and $R_3$ is a hydroxy-protecting group, and the protecting groups $R_1$, $R_3$ and, where appropriate, $R_2$ are then replaced by hydrogen. However, this method employs relatively harsh conditions, proceeds with poor conversion, and provides less than optimal yields.

A major difficulty remaining in the synthesis of taxol and other potential anti-tumor agents is the lack of a readily available method for easy attachment, to the C-13 oxygen, of the chemical unit which provides the $\beta$-amido ester side chain. Development of such a process for its attachment in high yield would facilitate the synthesis of taxol as well as related anti-tumor agents having a modified set of nuclear substituents or a modified C-13 side chain. This need has been fulfilled by the discovery of a new, efficient process for attachment, to the C-13 oxygen, of the chemical unit which provides the $\beta$-amido ester side chain.

SUMMARY OF THE INVENTION

Among the objects of the present invention, therefore, is the provision of a side chain precursor for the synthesis of taxane derivatives, and the provision of a process for the attachment of the side chain precursor in relatively high yield to provide an intermediate which is readily converted to the desired taxane derivative.

In accordance with the present invention, a process is provided for preparing taxol, taxotere and other biologwherein
$R_1$ is $-OR_6$;
$R_2$ is hydrogen, alkyl, alkenyl, alkynyl, aryl, or heteroaryl;
$R_3$ and $R_4$ are independently hydrogen, alkyl, alkenyl, alkynyl, aryl, heteroaryl, or acyl, provided, however, that $R_3$ and $R_4$ are not both acyl;
$R_5$ is alkyl, alkenyl, alkynyl, aryl, alkoxy, aryloxy or heteroaryloxy;
$R_6$ is hydrogen, alkyl, alkenyl, alkynyl, aryl, heteroaryl, or hydroxy protecting group,
$R_{15}$ and $R_{16}$ are independently hydrogen, hydroxy, lower alkanoyloxy, alkenoyloxy, alkynoyloxy, aryloyloxy or $R_{15}$ and $R_{16}$ together form an oxo;
$R_{17}$ and $R_{18}$ are independently hydrogen or lower alkanoyloxy, alkenoyloxy, alkynoyloxy, or aryloyloxy or $R_{17}$ and $R_{18}$ together form an oxo;
$R_{19}$ and $R_{20}$ are independently hydrogen or hydroxy or lower alkanoyloxy, alkenoyloxy, alkynoyloxy, or aryloyloxy;
$R_{21}$ and $R_{22}$ are independently hydrogen or lower alkanoyloxy, alkenoyloxy, alkynoyloxy, or aryloyloxy or $R_{21}$ and $R_{22}$ together form an oxo;
$R_{24}$ is hydrogen or hydroxy or lower alkanoyloxy, alkenoyloxy, alkynoyloxy, or aryloyloxy; or
$R_{23}$ and $R_{24}$ together form an oxo or methylene or $R_{23}$ and $R_{24}$ together form an oxirane ring or $R_{23}$ and $R_{22}$ together form an oxetane ring;
$R_{25}$ is hydrogen, hydroxy, or lower alkanoyloxy, alkenoyloxy, alkynoyloxy, or aryloyloxy or
$R_{26}$ is hydrogen, hydroxy, or lower alkanoyloxy, alkenoyloxy, alkynoyloxy, or aryloyloxy; or $R_{26}$ and $R_{25}$ taken together form an oxo; and
$R_{27}$ is hydrogen, hydroxy or lower alkoxy, alkanoyloxy, alkenoyloxy, alkynoyloxy, or aryloyloxy.

Briefly, therefore, the present invention is directed to a process for the preparation of a taxane derivative in which oxazinone (2) is reacted with a metal alkoxide having the bi-, tri- or tetracyclic taxane nucleus to form a $\beta$-amido ester intermediate. The intermediate is then converted to the taxane derivative. Oxazinone (2) has the general formula:

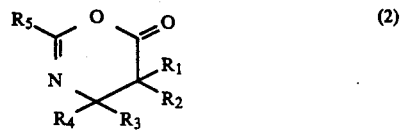

(2)

wherein $R_1$–$R_5$ are as previously defined. Preferably, the metal alkoxide has the tricyclic taxane nucleus corresponding to the general formula:

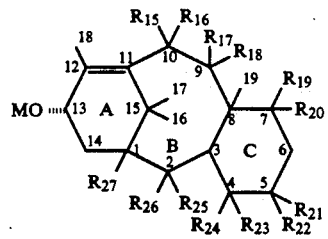

(3)

wherein M is a metal, and $R_{15}$-$R_{27}$ are as previously defined. Most preferably, the metal alkoxide has the tetracyclic taxane nucleus corresponding to metal alkoxide (3) wherein $R_{22}$ and $R_{23}$ together form an oxetane ring.

Other objects and features of this invention will be in part apparent and in part pointed out hereinafter.

DETAILED DESCRIPTION

The present invention is directed to a process for preparing taxol, taxotere and other taxane derivatives which are biologically active using oxazinone (2), the structure of which is depicted hereinbelow:

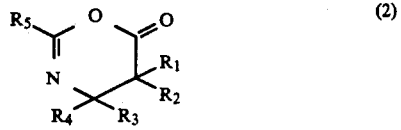

(2)

wherein $R_1$, $R_2$, $R_3$, $R_4$ and $R_5$ are as previously defined.

In accordance with the present invention, $R_5$ of oxazinone (2) is preferably aryl, p-substituted phenyl, or lower alkoxy, and most preferably phenyl, methoxy, ethoxy, tert-butoxy ("tBuO"; $(CH_3)_3CO$—), or

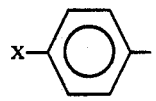

wherein X is Cl, Br, F, $CH_3O$—, or $NO_2$—. Preferably $R_2$ and $R_4$ are hydrogen or lower alkyl. $R_3$ is preferably aryl, most preferably, naphthyl, phenyl,

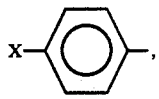

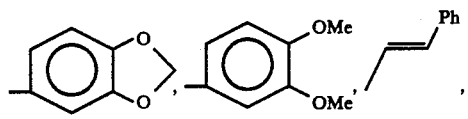

wherein X is as previously defined, Me is methyl and Ph is phenyl. Preferably, $R_1$ is —$OR_6$ wherein $R_6$ is 1-ethoxyethyl ("∓EE") methoxymethyl, or 2,2,2-trichloroethoxymethyl.

The oxazinone alkyl groups, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The oxazinone alkenyl groups, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, aryl, hexenyl, and the like.

The oxazinone alkynyl groups, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

The oxazinone aryl moieties described, either alone or with various substituents, contain from 6 to 15 carbon atoms and include phenyl, α-naphthyl or β-naphthyl, etc. Substituents include alkanoxy, protected hydroxy, halogen, alkyl, aryl, alkenyl, acyl, acyloxy, nitro, amino, amido, etc. Phenyl is the more preferred aryl As noted above, $R_1$ of oxazinone (2) is —$OR_6$ with $R_6$ being alkyl, acyl, 1-ethoxyethyl ("EE"), 2,2,2-trichloroethoxymethyl, or other hydroxyl protecting group such as acetals and ethers, i.e., methoxymethyl ("MOM"), benzyloxymethyl; and esters, such as acetates; carbonates, such as methyl carbonates. A variety of protecting groups for the hydroxyl group and the synthesis thereof may be found in "Protective Groups in Organic Synthesis" by T. W. Greene, John Wiley and Sons, 1981. The hydroxyl protecting group selected should be easily removed under conditions that are sufficiently mild, e.g., in 48% HF, acetonitrile, pyridine, or 0.5% HCl/water/ethanol, and/or zinc, acetic acid so as not to disturb the ester linkage or other substituents of the taxol intermediate. However, $R_6$ is preferably 1-ethoxyethyl or 2,2,2-trichloroethoxymethyl, and most preferably 1-ethoxyethyl.

Since oxazinone (2) has several asymmetric carbons, it is known to those skilled in the art that the compounds of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

Oxazinone (2) can be prepared from readily available materials according to the following reaction scheme:

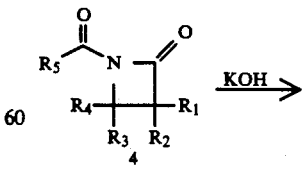

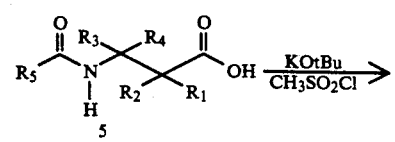

-continued

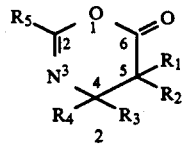

Carboxylic acid 5 may alternatively be prepared according to the method described in Greene et al., JACS 110, 5917 (1988). β-lactams 4 can be prepared from readily available materials, as illustrated in the following reaction scheme in which $R_3$ and $R_5$ are phenyl, $R_2$ and $R_4$ are hydrogen, and $R_2$ is —$OR_6$ wherein $R_6$ is ethoxyethyl:

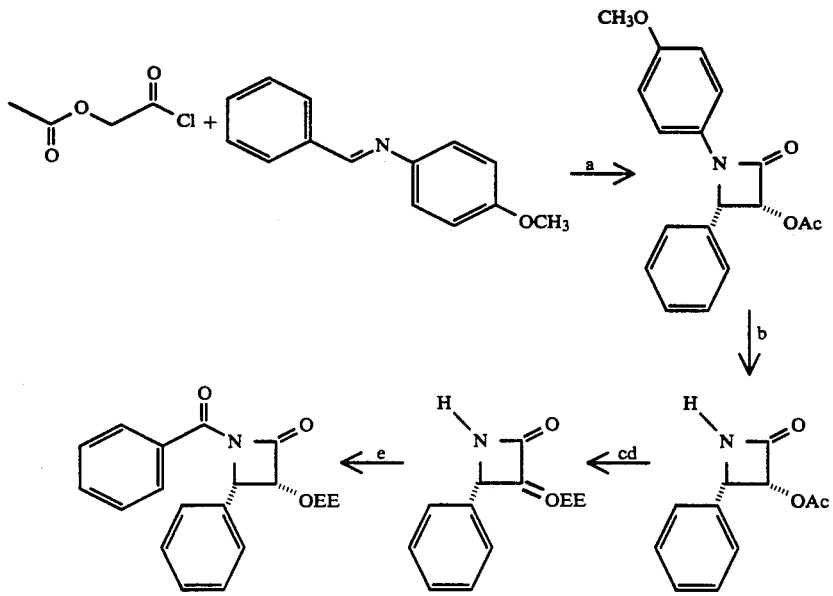

reagents: (a) triethylamine, $CH_2Cl_2$, 25° C., 18 h; (b) 4 equiv ceric ammonium nitrate, $CH_3CN$, −10° C., 10 min; (c) KOH, THF, H2O, 0° C., 30 min; (d) ethyl vinyl ether, THF, toluene sulfonic acid (cat.), 0° C., 1.5 h; (e) $CH_3Li$, ether, −78° C., 10 min; benzoyl chloride, −78° C., 1 h.

The starting materials are readily available. α-Acyloxy acetyl chloride is prepared from glycolic acid, and, in the presence of a tertiary amine, it cyclocondenses with imines prepared from aldehydes and p-methoxyaniline to give 1-p-methoxyphenyl-3-acyloxy-4-arylazetidin-2-ones.

The p-methoxyphenyl group can be readily removed through oxidation with ceric ammonium nitrate, and the acyloxy group can be hydrolyzed under standard conditions familiar to those experienced in the art to provide 3-hydroxy-4-arylazetidin-2-ones.

The 3-hydroxyl group may be protected with a variety of standard protecting groups such as the 1-ethoxyethyl group. Preferably, the racemic 3-hydroxy-4-arylazetidin-2-one is resolved into the pure enantiomers prior to protection by recrystallization of the corresponding 2-methoxy-2-(trifluoromethyl) phenylacetic esters and only the dextrorotatory enantiomer is used in the preparation of taxol. In any event, the 3-(1-ethoxyethoxy)-4-phenylazetidin-2-one can be converted to β-lactam 4, by treatment with a base, preferably n-butyllithium, and an aroyl chloride at −78° C. or below.

As noted above, the metal alkoxides used in the process of the present invention have the bi-, tri- or tetracyclic taxane nucleus. As used herein, a metal alkoxide having the bicyclic taxane nucleus corresponds to a compound containing rings A and B of metal alkoxide (3):

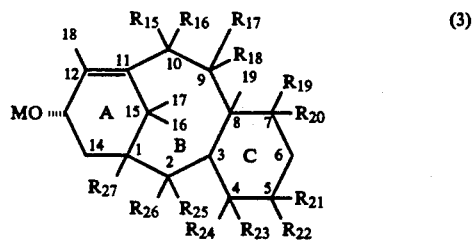

wherein M and $R_{15}$–$R_{27}$ are as previously defined. A metal alkoxide having the tricyclic taxane nucleus corresponds to a compound containing rings A, B and C of metal alkoxide (3). A metal alkoxide having the tetracyclic taxane nucleus corresponds to a compound containing rings A, B and C of metal alkoxide (3) and in which $R_{22}$ and $R_{23}$ together form an oxetane ring.

Preferably, the metal alkoxide used in the process of the present invention is metal alkoxide (3). Most preferably, $R_{15}$ is —$OT_2$ or —$OCOCH_3$; $R_{16}$ is hydrogen; $R_{17}$ and $R_{18}$ together form an oxo; $R_{19}$ is —$OT_1$; $R_{20}$ and $R_{21}$ are hydrogen; $R_{22}$ and $R_{23}$ together form an oxetane ring; $R_{24}$ is $CH_3COO$—; $R_{25}$ is PhCOO—; $R_{26}$ is hydrogen; $R_{27}$ is hydroxy; and $T_1$ and $T_2$ are independently hydrogen or hydroxy protecting group. The metal alkoxide hydroxy protecting groups may be the same as those previously identified for $R_6$ of the oxazinone, and preferably are trialkyl or triaryl silyl, and most preferably, triethyl silyl ("TES").

Metal substituent, M, of metal alkoxide (3) is a Group IA, IIA, IIIA, lanthanide or actinide element or a transition, Group IIIA, IVA, VA or VIA metal. Preferably, it is a Group IA, IIA or transition metal, and most preferably, it is lithium, magnesium, sodium, potassium or titantium.

The metal alkoxide alkyl groups, either alone or with the various substituents defined hereinabove are preferably lower alkyl containing from one to six carbon atoms in the principal chain and up to 10 carbon atoms. They may be straight or branched chain and include methyl, ethyl, propyl, isopropyl, butyl, isobutyl, tert-butyl, aryl, hexyl, and the like.

The metal alkoxide alkenyl groups, either alone or with the various substituents defined hereinabove are preferably lower alkenyl containing from two to six carbon atoms in the principal chain and up to 10 carbon atoms. They may be straight or branched chain and include ethenyl, propenyl, isopropenyl, butenyl, isobutenyl, aryl, hexenyl, and the like.

The metal alkoxide alkynyl groups, either alone or with the various substituents defined hereinabove are preferably lower alkynyl containing from two to six carbon atoms in the principal chain and up to 10 carbon atoms. They may be straight or branched chain and include ethynyl, propynyl, butynyl, isobutynyl, aryl, hexynyl, and the like.

Exemplary alkanoyloxy include acetate, propionate, butyrate, valarate, isobutyrate and the like. The more preferred alkanoyloxy is acetate.

The metal alkoxide aryl moieties, either alone or with various substituents contain from 6 to 10 carbon atoms and include phenyl, α-naphthyl or β-naphthyl, etc. Substituents include alkanoxy, hydroxy, halogen, alkyl, aryl, alkenyl, acyl, acyloxy, nitro, amino, amido, etc. Phenyl is the more preferred aryl.

Metal alkoxides (3) are prepared by reacting an alcohol having two to four rings of the taxane nucleus and a C-13 hydroxyl group with an organometallic compound in a suitable solvent. Preferably, the alcohol is derivative of baccatin III or 10-deacetyl baccatin III having the structure

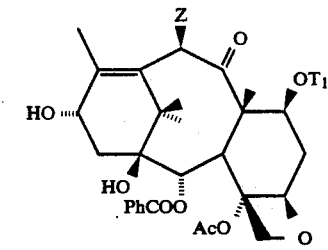

(6)

wherein $T_1$ is a hydroxy protecting group, and Z is $-OT_2$ wherein $T_2$ is acyl, preferably acetyl, or hydroxy protecting group. Most preferably, the alcohol is a protected baccatin III, in particular, 7-O-triethylsilyl baccatin III (which can be obtained as described by Greene, et al. in JACS 110, 5917 (1988) or by other routes) or 7,10-bis-O-triethylsilyl baccatin III.

As reported in Greene et al., 10-deacetyl baccatin III is converted to 7-O-triethylsilyl-10-deacetyl baccatin III according to the following reaction scheme:

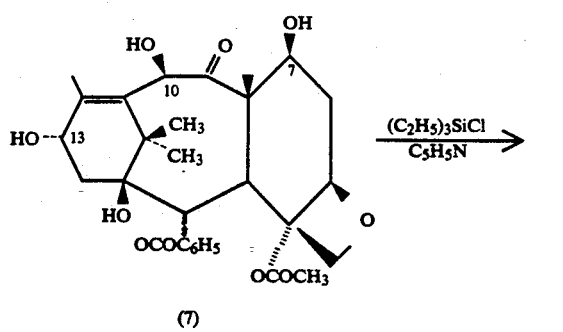

(7)

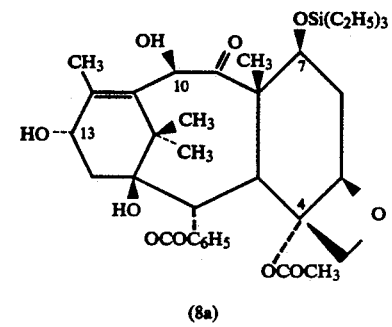

(8a)

Under what is reported to be carefully optimized conditions, 10-deacetyl baccatin III is reacted with 20 equivalents of $(C_2H_5)_3SiCl$ at 23° C. under an argon atmosphere for 20 hours in the presence of 50 ml of pyridine/mmol of 10-deacetyl baccatin III to provide 7-triethylsilyl-10-deacetyl baccatin III (8a) as a reaction product in 84–86% yield after purification. The reaction product is then acetylated with 5 equivalents of $CH_3COCl$ and 25 mL of pyridine/mmol of (8a) at 0° C. under an argon atmosphere for 48 hours to provide 86% yield of 7-O-triethylsilyl baccatin III (8b). Greene, et al. in JACS 110, 5917 at 5918 (1988).

Alternatively, 7-triethylsilyl-10-deacetyl baccatin III (8a) can be protected at C-10 oxygen with an acid labile hydroxyl protecting group. For example, treatment of (8a) with n-butyllithium in THF followed by triethylsilyl chloride (1.1 mol equiv.) at 0° C. gives 7,10-bis-O-triethylsilyl baccatin III (8c) in 95% yield. Also, (8a) can be converted to 7-O-triethylsilyl-10-(1-ethoxyethyl) baccatin III (8d) in 90% yield by treatment with excess ethyl vinyl ether and a catalytic amount of methane sulfonic acid. These preparations are illustrated in the reaction scheme below.

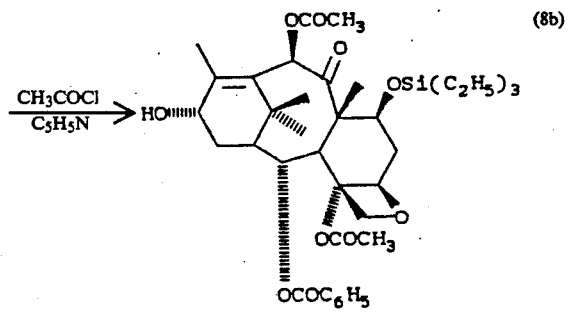

(8b)

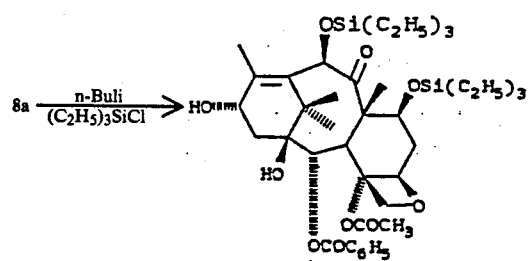

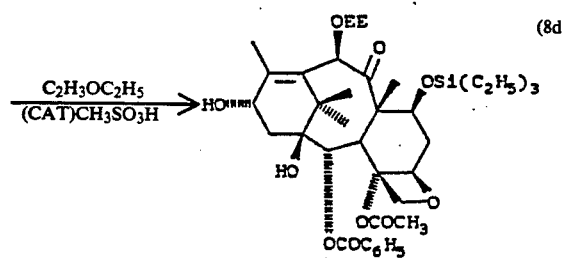

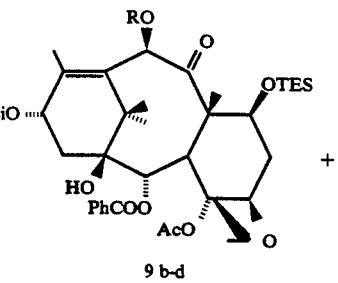

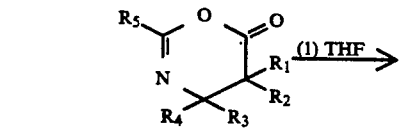

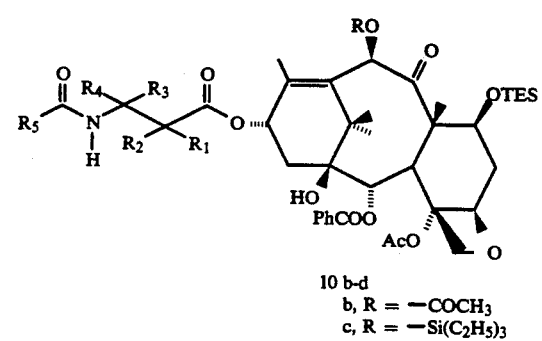

10 b-d
b, R = —COCH₃
c, R = —Si(C₂H₅)₃
d, R = —EE

7-O-triethylsilyl baccatin III (8b), 7,10-bis-O-triethylsilyl baccatin III (8c), or 7-O-triethylsilyl-10-(1-ethoxyethyl) baccatin III (8d), is reacted with an organometallic compound such as n-butyllithium in a solvent such as tetrahydrofuran (THF), to form the metal alkoxide 13-O-lithium-7-O-triethylsilyl baccatin III (9b) 13-O-lithium-7,10-bis-O-triethylsilyl baccatin III (9c), or 13-O-lithium-7-O-triethylsilyl-10- (1-ethoxyethyl) baccatin III (9d) as shown in the following reaction scheme:

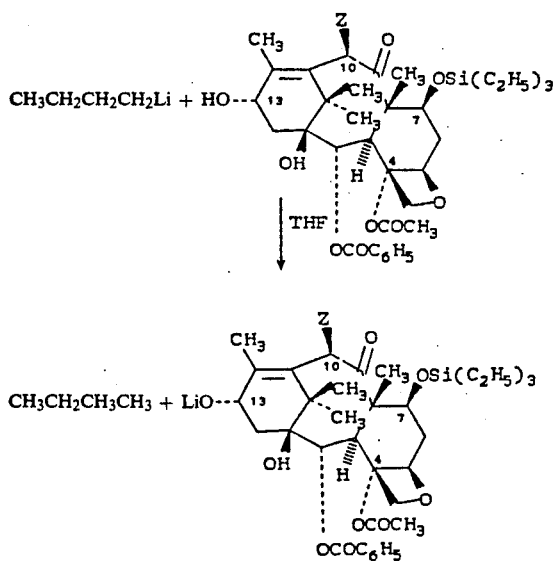

(9b) Z = —OCOCH₃
(9c) Z = —OSi(C₂H₅)₃
(9d) Z = —OEE

As illustrated in the following reaction scheme, a suitable metal alkoxide of the present invention such as 13-O-lithium-7-O-triethylsilyl baccatin III derivative (9b, 9c, or 9d) reacts with an oxazinone of the present invention to provide an intermediate (10b, 10c, or 10d) in which the C-7 hydroxyl group is protected with a triethylsilyl or 1-ethoxyethyl group.

Intermediate compound (10b) readily converts to taxol when R₁ is —OR₆, R₂ and R₃ are hydrogen, R₄ is phenyl, R₅ is benzoyl and R₆ is a hydroxy protecting group such as 1-ethoxyethyl. Intermediate compound (10c) readily converts to taxotere when R₁ is —OR₆, R₂ and R₃ are hydrogen, R₄ is phenyl, R₅ is tertbutoxycarbonyl and R₆ is a hydroxy protecting group such as 1-ethoxyethyl. Intermediate compound (10d) readily converts to 10-deacetyl taxol when R₁ is —OR₆, R₂ and R₃ are hydrogen, R₄ is phenyl, R₅ is benzoyl, and R₆ is a hydroxy protecting group such as 1-ethoxyethyl. Intermediate compounds (10b, 10c and 10d) may be converted to the indicated compounds by hydrolyzing the triethylsilyl and 1-ethoxyethyl groups under mild conditions so as not to disturb the ester linkage or the taxane derivative substituents.

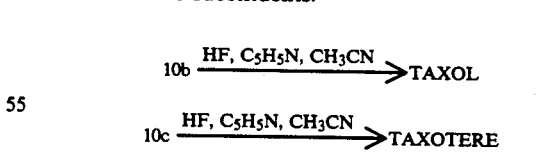

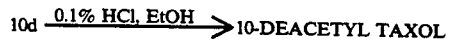

Other taxane derivatives may readily be prepared by selection of the proper substituents R₁-R₅ of oxazinone (2) or R₁₅-R₂₇ of metal alkoxide (3). The preparation of such other compounds is illustrated in the examples which follow.

Both the conversion of the alcohol to the metal alkoxide and the ultimate synthesis of the taxol can take place in the same reaction vessel. Preferably, the oxazinone is added to the reaction vessel after formation therein of the metal alkoxide.

The organometallic compound n-butyllithium is preferably used to convert the alcohol to the corresponding metal alkoxide, but other sources of metallic substituent such as lithium diisopropyl amide, other lithium or magnesium amides, ethylmagnesium bromide, methylmagnesium bromide, other organolithium compounds, other organomagnesium compounds, organosodium, organotitanium or organopotassium may also be used. Organometallic compounds are readily available, or may be prepared by available methods including reduction of organic halides with metal. For example, butyl bromide can be reacted with lithium metal in diethyl ether to give a solution of n-butyllithium in the following manner:

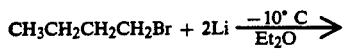

$$CH_3CH_2CH_2CH_2Li + LiBr$$

Although THF is the preferred solvent for the reaction mixture, other ethereal solvents, such as dimethoxyethane, or aromatic solvents may also be suitable. Certain solvents, including some halogenated solvents and some straight-chain hydrocarbons in which the reactants are too poorly soluble, are not suitable. Other solvents are not appropriate for other reasons. For example, esters are not appropriate for use with certain organometallic compounds such as n-butyllithium due to incompatibility therewith.

Although the reaction scheme disclosed herein is directed to the synthesis of certain taxane derivatives, it can be used with modifications in either the oxazinone or the tetracyclic metal alkoxide. Therefore metal alkoxides other than 13-O-lithium-7-O-triethylsilyl baccatin III may be used to form an intermediate according to the method of this invention. The oxazinone and the tetracyclic metal alkoxide can be derived from natural or unnatural sources, to prepare other synthetic taxols, taxol derivatives, 10-deacetyltaxols, and the enantiomers and diastereomers thereof contemplated within the present invention.

The water solubility of compounds of formula (1) may be improved if $R_1$ is $—OR_6$ and $R_{19}$ is $—OT_1$, and $R_6$ and/or $T_1$ are a functional group which increases solubility, such as $—COGCOR^1$ wherein G is ethylene, propylene, CHCH—, 1,2-cyclohexane, or 1,2-phenylene, $R^1$ = OH base $NR^2R^3$, $OR^3$, $SR^3$, $OCH_2CONR^4R^5$, OH $R^2$ = hydrogen, methyl $R^3 = (CH_2)_nNR^6R^7$; $(CH_2)_nN\oplus R^6R^7R^8X_1\sigma$ n = 1 to 3

$R^4$ = hydrogen, lower alkyl containing 1 to 4 carbons $R^5$ = hydrogen, lower alkyl containing 1 to 4 carbons, benzyl, hydroxyethyl, $CH_2CO_2H$, dimethylaminoethyl $R^6R^7$ = lower alkyl containing 1 or 2 carbons, benzyl or $R^6$ and $R^7$ together with the nitrogen atom of $NR^6R^7$ form the following rings

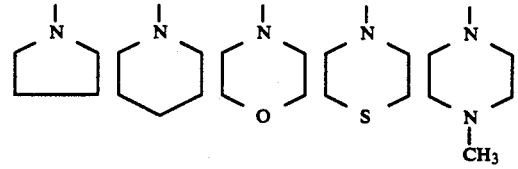

$R^8$ = lower alkyl containing 1 or 2 carbons, benzyl $X_1^\ominus$ = halide base = $NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

The preparation of compounds in which $R_6$ or $T_1$ is $—COGCOR^1$ is set forth in Haugwitz U.S. Pat. No. 4,942,184 which is incorporated herein by reference.

The following examples illustrate the invention.

EXAMPLE 1

Preparation of Taxol

To a solution of 7-triethylsilyl baccatin III (100 mg, 0.143 mmol) in 1 mL of THF at −45° C. was added dropwise 0.087 mL of a 1.63M solution of nBuLi in hexane. After 1 h at −45° C., a solution of 92 mg (0.286 mmol) of (−)-cis-2,4-diphenyl-5-(1-ethoxyethoxy)-4,5-dihydro-1,3-oxazin-6-one in 1 mL of THF was added dropwise to the mixture. The solution was warmed to 0° C. and kept at that temperature for 2 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by flash chromatography followed by recrystallization to give 120 mg (80%) of (2'R,3'S)-2'-ethoxyethyl-7-triethylsilyl taxol.

A 5 mg sample of (2'R,3'S)-2'-ethoxyethyl-7-triethylsilyl taxol was dissolved in 2 mL of ethanol and 0.5 mL of 0.5% aqueous HCl solution was added. The mixture was stirred at 0° C. for 30 h and diluted with 50 mL of ethyl acetate. The solution was extracted with 20 mL of saturated aqueous sodium bicarbonate solution, dried over sodium sulfate and concentrated. The residue was purified by flash chromatography to provide 4.5 mg (ca. 90%) of taxol, which was identical with an authentic sample in all respects.

EXAMPLE 2

Preparation of N-debenzoyl-N-tertbutoxycarbonyl-10-deacetyl Taxol (Taxotere)

2-tertbutoxy-4-phenyl-5-(1-ethoxyethoxy)-4,5-dihydro-1,3-oxazin-6-one. To a solution of 409 mg (1.16 mmol) of N-tertbutoxycarbonyl-O-(1-ethoxyethyl)-3-phenylisoserine (3) in 20 mL of THF was added 261 mg (2.33 mmol) of solid potassium tert-butoxide and the mixture was stirred at 25° C. for 30 min. A solution of 134 mg (1.16 mmol) of methanesulfonyl chloride in 3.2 mL of THF was added and the mixture was stirred at 25° C. for 1.5 h. The mixture was diluted with 80 mL of hexane and ethyl acetate and this solution was extracted with 20 mL of saturated aqueous sodium bicarbonate solution and 10 mL of brine. The organic phase was dried over sodium sulfate and concentrated to give 235 mg (70%) of 2-tertbutoxy-4-phenyl-5-(1-ethoxyethoxy)-4,5-dihydro-1,3-oxazin-6-one as a colorless oil.

N-debenzoyl-N-tertbotoxycarbonyl-10-deacetyl-Taxol (Taxotere). To a solution of 7,10-bis-treithylsilyl baccatin III (100 mg, 0.124 mmol)) in 1 mL of THF at −45° C. was added dropwise 0.087 ml of a 1.63M solution of nBuLi in hexane. After 1 h at −45° C., a solution of 88 mg (0.286 mmol) of (−)-cis-2-tertbutoxy-4-phenyl-5-(1-ethoxyethoxy)-4,5-dihydro-1,3-oxazin-6-one in 1 mL of THF was added dropwise to the mixture. The solution was warmed to 0° C. and kept at that temperature for 2 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by flash chromatography followed by recrystallization to give 120 mg (80%) of (2'R,3'S)-N-debenzoyl-N-tertbutoxycarbonyl-2'-ethoxyethyl-7,10-bis-treithylsilyl taxol.

A 5 mg sample of (2'R,3'S)-N-debenzoyl-N-tertbutoxycarbonyl-2'-ethoxyethyl-7,10-bis-triethylsilyl taxol was dissolved in 2 mL of ethanol and 0.5 mL of 0.5% aqueous HCl solution was added. The mixture was stirred at 0° C. for 30 h and diluted with 50 mL of ethyl acetate. The solution was extracted with 20 mL of saturated aqueous sodium bicarbonate solution, dried over sodium sulfate and concentrated. The residue was purified by column chromatography on silica gel eluted with ethyl/hexane to provide 3.8 mg (ca. 90%) of N-debenzoyl-N-tertbutoxycarbonyl-10-deacetyl Taxol (Taxotere). All analytical and spectral data were identical with that reported for taxotere in U.S. Pat. No. 4,814,470.

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

What I claim is:

1. A process for the preparation of a taxane derivative comprising:

providing a metal alkoxide having the tetracyclic taxane nucleus, the metal being a Group IA, IIA, IIIA, IVA, VA, VIA or transition metal and is attached to the oxygen at the C-13 position of the nucleus, reacting the metal alkoxide with an oxazinone to form an intermediate, wherein the oxazinone has the formula:

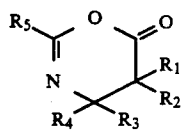
(2)

wherein $R_1$ is $-OR_6$;

$R_2$ is hydrogen, alkyl, alkenyl, alkynyl, aryl, or heteroaryl;

$R_3$ and $R_4$ are independently hydrogen, alkyl, alkenyl, alkynyl, aryl, heteroaryl, or acyl, provided, however, that $R_3$ and $R_4$ are not both acyl;

$R_5$ is alkyl, alkenyl, alkynyl, aryl, alkoxy, aryloxy or heteroaryloxy; and $R^6$ is a hydroxy protecting group; and converting said intermediate to the taxane derivative by removing the hydroxy protecting group.

2. The process of claim 1 wherein $R_2$ and $R_4$ are hydrogen or lower alkyl, $R_3$ is aryl, and $R_6$ is a hydroxy protecting group.

3. The process of claim 2 wherein $R_3$ is phenyl and $R_6$ is 1-ethoxyethyl or 2,2,2-trichloroethoxymethyl.

4. The process of claim 1 wherein the metal alkoxide is a meal alkoxide of 7-protected baccatin III.

5. The process of claim 4 wherein the metallic oxide substituent is selected from the group of metal substituents consisting of LiO—, MgO NaO—, KO—, and TiO—.

6. The process of claim 1 wherein the metal alkoxide is derived from an alcohol having the formula:

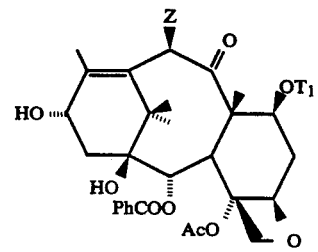
(4)

wherein $T_1$ is a hydroxy protecting group, Z is $-OT_2$, and $T_2$ is acetyl or hydroxy protecting group.

7. The process of claim 1 wherein the metal alkoxide has the following formula:

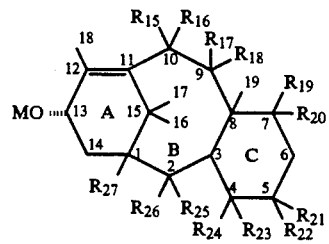
(3)

wherein:

$R_{15}$ and $R_{16}$ are independently hydrogen, hydroxy, lower alkanoyloxy, alkenoyloxy, alkynoyloxy, aryloyloxy or $R_{15}$ and $R_{16}$ together form an oxo;

$R_{17}$ and $R_{18}$ are independently hydrogen or lower alkanoyloxy, alkenoyloxy, alkynoyloxy, or aryloyloxy or $R_{17}$ and $R_{18}$ together form an oxo;

$R_{19}$ and $R_{20}$ are independently hydrogen or hydroxy or lower alkanoyloxy, alkenoyloxy, alkynoyloxy, or aryloyloxy;

$R_{21}$ and $R_{22}$ are independently hydrogen or lower alkanoyloxy, alkenoyloxy, alkynoyloxy, or aryloyloxy or $R_{21}$ and $R_{22}$ together form an oxo;

$R_{24}$ is hydrogen or hydroxy or lower alkanoyloxy, alkenoyloxy, alkynoyloxy, or aryloyloxy; or $R_{23}$ and $R_{22}$ together form an oxetane ring;

$R_{25}$ is hydrogen, hydroxy, or lower alkanoyloxy, alkenoyloxy, alkynoyloxy, or aryloyloxy or $R_{26}$ is hydrogen, hydroxy, or lower alkanoyloxy, alkenoyloxy, alkynoyloxy, or aryloyloxy; or $R_{26}$ and $R_{25}$ taken together form an oxo; and $R_{27}$ is hydrogen, hydroxy or lower alkoxy, alkanoyloxy, alkenoyloxy, alkynoyloxy, or aryloyloxy.

8. The process of claim 7 wherein $R_{16}$ is hydrogen, $R_{15}$ is $-OT_2$ or $-OCOCH_3$, $T_2$ is a hydroxy protecting group and M is selected from the group comprising Li, Mg, Na, K and Ti.

9. The process of claim 7 wherein $R_2$ and $R_4$ are hydrogen or lower alkyl, $R_3$ is aryl, and $R_6$ is a hydroxy protecting group.

10. A process for the preparation of a taxane derivative comprising:

providing a metal alkoxide having the tetracyclic taxane nucleus, the metal being a Group IA, IIA, IIIA, IVA, VA, VIA or transition metal and is attached to the oxygen at the C-13 position of the nucleus, reacting the metal alkoxide with the oxazinone to form an intermediate, wherein the oxazinone has the formula:

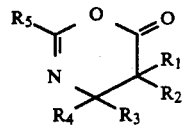

(2)

wherein $R_1$ is $-OR_6$;

$R_2$ is hydrogen;

$R_3$ and $R_4$ are independently hydrogen, alkyl, alkenyl, alkynyl, aryl, heteroaryl, or acyl, provided, however, that $R_3$ and $R_4$ are not both acyl;

$R_5$ is alkyl, alkenyl, alkynyl, aryl, alkoxy, aryloxy or heteroaryloxy; and $R^6$ is a hydroxy protecting group; and converting said intermediate to the taxane derivative by removing the hydroxy protecting group.

11. The process of claim 10 wherein $R_6$ is 1-ethoxyethyl or 2,2,2-trichloroethoxymethyl.

12. The process of claim 10 wherein the metal alkoxide is derived from an alcohol having the formula:

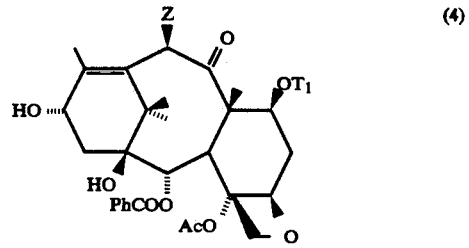

(4)

wherein $T_1$ is a hydroxy protecting group, Z is $-OT_2$, and $T_2$ is acetyl or hydroxy protecting group.

13. The process of claim 10 wherein $R_{16}$ is hydrogen, $R_{15}$ is $-OT_2$ or $-OCOCH_3$, $T_2$ is a hydroxy protecting group and M is selected from the group comprising Li, Mg, Na, K and Ti.

* * * * *

UNITED STATES PATENT AND TRADEMARK OFFICE
CERTIFICATE OF CORRECTION

PATENT NO. : 5,254,703

DATED : October 19, 1993

INVENTOR(S) : Robert A. Holton

It is certified that error appears in the above-identified patent and that said Letters Patent is hereby corrected as shown below:

In column 1, following the Title of the Invention please insert the following paragraph:
-- This invention was made with Government support under NIH Grant #CA 42031 awarded by the National Institutes of Health. The Government has certain rights in the invention. --

Column 2, lines 20-30, the chemical should read

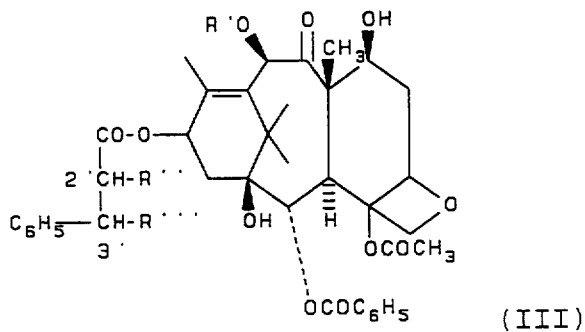

(III)

UNITED STATES PATENT AND TRADEMARK OFFICE
CERTIFICATE OF CORRECTION

PATENT NO. : 5,254,703
DATED : October 19, 1993
INVENTOR(S) : Robert A. Holton It is certified that error appears in the above-identified patent and that said Letters Patent is hereby corrected as shown below:

Column 2, lines 43-50, the chemical should read

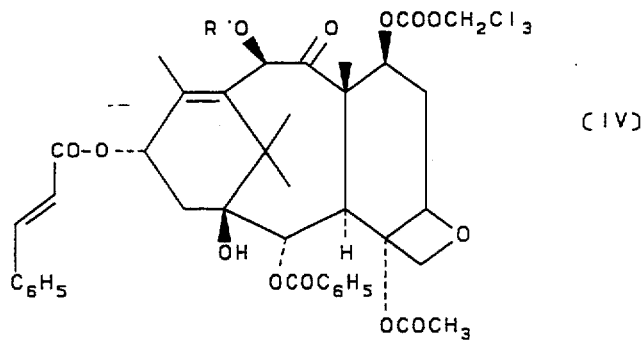

Column 3, lines 3-12, the chemical should read

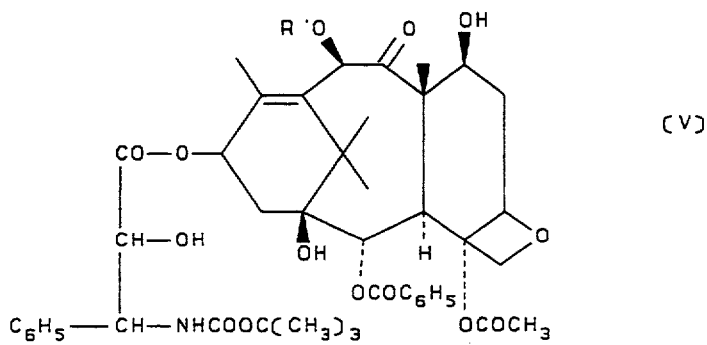

UNITED STATES PATENT AND TRADEMARK OFFICE
CERTIFICATE OF CORRECTION

PATENT NO. : 5,254,703
DATED : October 19, 1993
INVENTOR(S) : Robert A. Holton It is certified that error appears in the above-identified patent and that said Letters Patent is hereby corrected as shown below:

Column 3, lines 28-38, the chemical should read

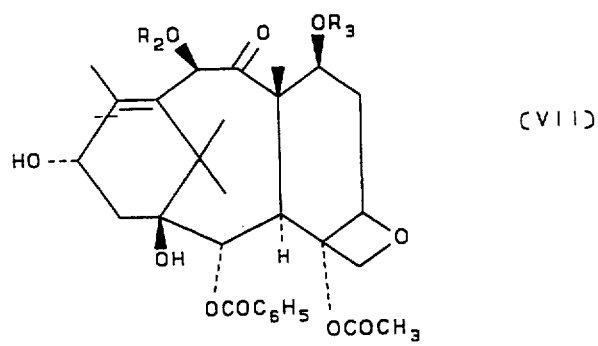

(VII)

Column 4, lines 5-13, the chemical should read

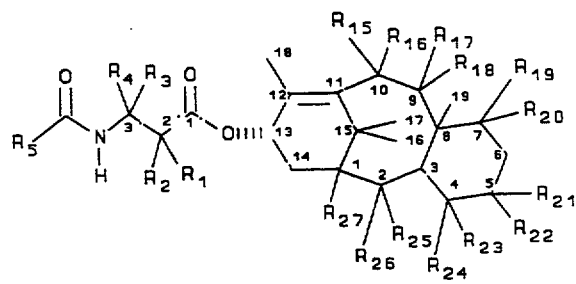

Column 5, line 65, "(∓EE")" should read --("EE")-- .

UNITED STATES PATENT AND TRADEMARK OFFICE
CERTIFICATE OF CORRECTION

PATENT NO. : 5,254,703
DATED : October 19, 1993
INVENTOR(S) : Robert A. Holton

It is certified that error appears in the above-identified patent and that said Letters Patent is hereby corrected as shown below:

Column 8, lines 8-15, the chemical should read

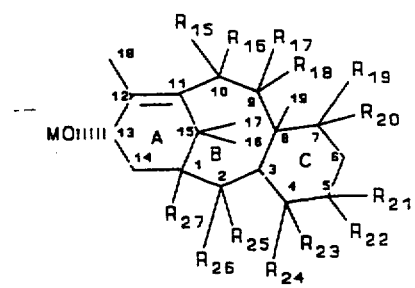

Column 10, lines 17-25, chemical (8a) should read

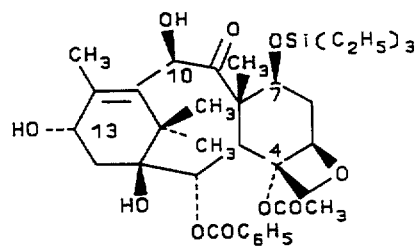

UNITED STATES PATENT AND TRADEMARK OFFICE
CERTIFICATE OF CORRECTION

PATENT NO. : 5,254,703
DATED : October 19, 1993
INVENTOR(S) : Robert A. Holton It is certified that error appears in the above-identified patent and that said Letters Patent is hereby corrected as shown below:

Column 10, lines 60-68, chemical (8b) should read

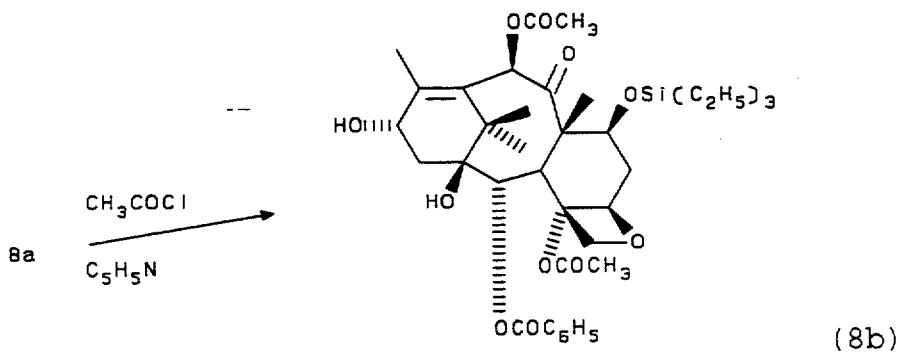

Column 11, lines 15-23, chemical (8d) should read

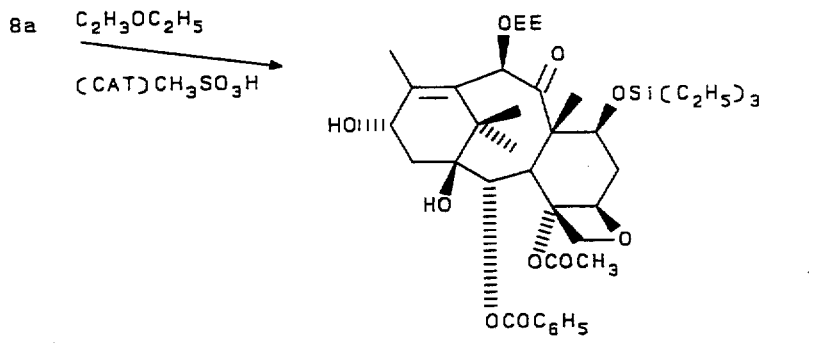

UNITED STATES PATENT AND TRADEMARK OFFICE
CERTIFICATE OF CORRECTION

Page 6 of 8

PATENT NO. : 5,254,703
DATED : October 19, 1993
INVENTOR(S) : Robert A. Holton

It is certified that error appears in the above-identified patent and that said Letters Patent is hereby corrected as shown below:

Column 11, lines 38-56, the chemical should read

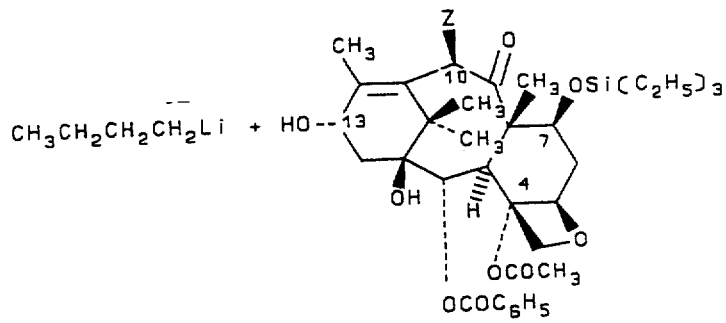

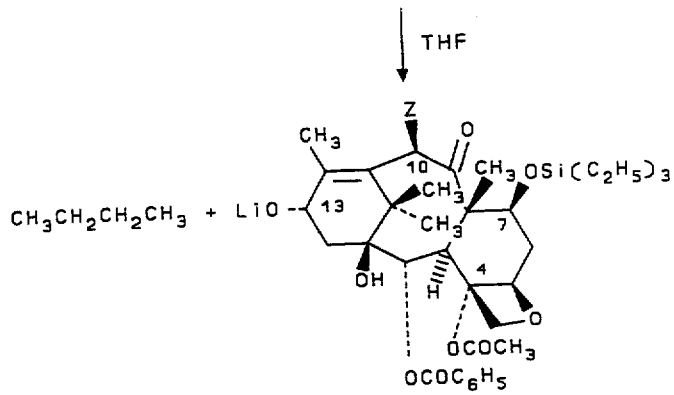

UNITED STATES PATENT AND TRADEMARK OFFICE
CERTIFICATE OF CORRECTION

PATENT NO. : 5,254,703
DATED : October 19, 1993
INVENTOR(S) : Robert A. Holton

It is certified that error appears in the above-identified patent and that said Letters Patent is hereby corrected as shown below:

Column 12, lines 1-12, chemical 9 b-d should read

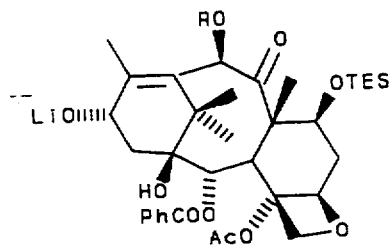

Column 13, line 53, "CHCH-" should read -- -CHCH- --.

Column 13, line 58, "$(CH_2)_nN\oplus R^6R^7R^8X_1\sigma$" should read --$(CH_2)_nN^{\oplus}R^6R^7R^8X_1^{\ominus}$--.

Column 15, line 2, "treithylsilyl" should read --triethylsilyl--.

UNITED STATES PATENT AND TRADEMARK OFFICE
CERTIFICATE OF CORRECTION

PATENT NO. : 5,254,703

DATED : October 19, 1993

INVENTOR(S) : Robert A. Holton

It is certified that error appears in the above-identified patent and that said Letters Patent is hereby corrected as shown below:

Column 15, line 17, "treithylsilyl" should read --triethylsilyl--.

Claim 4 in column 16, line 9, "meal" should read --metal--.

Signed and Sealed this

Thirtieth Day of July, 1996

BRUCE LEHMAN

Attest:

*Attesting Officer*           *Commissioner of Patents and Trademarks*